US012584578B2

(12) United States Patent
Austin et al.

(10) Patent No.: US 12,584,578 B2
(45) Date of Patent: Mar. 24, 2026

(54) TORSIONAL CONNECTOR COUPLING ASSEMBLY

(71) Applicant: CareFusion 303, Inc., San Diego, CA (US)

(72) Inventors: Abin Austin, Thrissur (IN); Mohammed Mehtab Khan, Bengaluru (IN); Aman Desai, Bengaluru (IN)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/595,982

(22) Filed: Mar. 5, 2024

(65) Prior Publication Data

US 2024/0328555 A1     Oct. 3, 2024

Related U.S. Application Data

(60) Provisional application No. 63/454,884, filed on Mar. 27, 2023.

(51) Int. Cl.
*F16L 37/367*     (2006.01)
*A61M 39/10*     (2006.01)
(Continued)

(52) U.S. Cl.
CPC ........... *F16L 37/367* (2013.01); *A61M 39/22* (2013.01); *A61M 2039/1027* (2013.01); *A61M 39/26* (2013.01); *F16L 37/02* (2013.01)

(58) Field of Classification Search
CPC .. A61M 39/22; A61M 39/26; A61M 39/1011; A61M 2039/226;
(Continued)

(56) References Cited

U.S. PATENT DOCUMENTS

| | | | | |
|---|---|---|---|---|
| 206,009 A | * | 7/1878 | Fogerty | F16L 37/252 251/149 |
| 983,259 A | * | 1/1911 | Roth et al. | B65D 51/1683 217/99 |

(Continued)

FOREIGN PATENT DOCUMENTS

| | | |
|---|---|---|
| EP | 1678070 A2 | 7/2006 |
| EP | 1517723 B1 | 1/2007 |

(Continued)

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.
(Continued)

*Primary Examiner* — Kenneth Rinehart
*Assistant Examiner* — Jonathan J Waddy
(74) *Attorney, Agent, or Firm* — MASCHOFF BRENNAN

(57)     ABSTRACT

A coupler including a first connector having a mating portion with a first opening, and a first torsion member disposed within the mating portion with a first channel. The first torsion member being rotatable relative to the mating portion. The coupler including a second connector having a second torsion member with a second channel, and a coupling portion having a second opening and at least partially disposed within the second torsion member. The second torsion member configured to couple to the first torsion member to couple the first connector to the second connector such that rotation of the second torsion member causes rotation of the first torsion member to cause alignment of the first channel, the first opening, the second channel, and the second opening to form a fluid pathway. The first connector
(Continued)

FIG. 6C is configured to decouple from the second connector in response to a force exceeding a threshold force.

19 Claims, 10 Drawing Sheets

(51) Int. Cl.
    *A61M 39/22*     (2006.01)
    *A61M 39/26*     (2006.01)
    *F16L 37/02*     (2006.01)

(58) Field of Classification Search
    CPC .. A61M 2039/1016; A61M 2039/1027; A61M
            2039/229; A61M 2039/265; F16L 37/252;
            F16L 37/28; F16L 37/30; F16L 37/367;
                        F16L 37/02; F16L 37/373
    USPC ........................................................ 251/149
    See application file for complete search history.

(56) References Cited

U.S. PATENT DOCUMENTS

| | | | |
|---|---|---|---|
| 2,317,827 | A * | 4/1943 | Townhill ............... F16L 37/367 |
| | | | 137/614.01 |
| 4,588,504 | A * | 5/1986 | Berges .................. F16L 37/367 |
| | | | 210/234 |
| 5,607,582 | A * | 3/1997 | Yamazaki ............ B01D 35/153 |
| | | | 210/234 |
| 5,713,856 | A | 2/1998 | Eggers et al. |
| 5,947,954 | A | 9/1999 | Bonaldo |
| 6,874,522 | B2 | 4/2005 | Anderson et al. |
| 7,004,934 | B2 | 2/2006 | Vaillancourt |
| 7,040,598 | B2 | 5/2006 | Raybuck |
| 7,153,296 | B2 | 12/2006 | Mitchell |
| 7,350,764 | B2 | 4/2008 | Raybuck |
| 7,396,051 | B2 | 7/2008 | Baldwin et al. |
| 7,763,013 | B2 | 7/2010 | Baldwin et al. |
| 7,766,394 | B2 | 8/2010 | Sage et al. |
| 7,794,675 | B2 | 9/2010 | Lynn |
| 7,803,139 | B2 | 9/2010 | Fangrow, Jr. |
| 7,803,140 | B2 | 9/2010 | Fangrow, Jr. |
| 7,815,614 | B2 | 10/2010 | Fangrow, Jr. |
| 7,918,243 | B2 | 4/2011 | Diodati et al. |
| 7,998,134 | B2 | 8/2011 | Fangrow et al. |
| 8,123,738 | B2 | 2/2012 | Vaillancourt |
| 8,142,418 | B2 | 3/2012 | Mcmichael et al. |
| 8,211,069 | B2 | 7/2012 | Fangrow, Jr. |
| 8,262,628 | B2 | 9/2012 | Fangrow, Jr. |
| 8,361,408 | B2 | 1/2013 | Lynn |
| 8,480,968 | B2 | 7/2013 | Lynn |
| 8,777,908 | B2 | 7/2014 | Fangrow, Jr. |
| 8,777,909 | B2 | 7/2014 | Fangrow, Jr. |
| 8,795,256 | B1 | 8/2014 | Smith |
| 8,888,758 | B2 | 11/2014 | Mansour |
| 8,899,267 | B2 | 12/2014 | Diodati et al. |
| 8,910,919 | B2 | 12/2014 | Bonnal et al. |
| 8,974,425 | B2 | 3/2015 | Tachizaki et al. |
| 8,974,437 | B2 | 3/2015 | Williams et al. |
| 9,114,242 | B2 | 8/2015 | Fangrow et al. |
| 9,126,028 | B2 | 9/2015 | Fangrow et al. |
| 9,126,029 | B2 | 9/2015 | Fangrow et al. |
| 9,192,753 | B2 | 11/2015 | Lopez et al. |
| 9,234,616 | B2 | 1/2016 | Carrez et al. |
| 9,358,379 | B2 | 6/2016 | Fangrow, Jr. |
| 9,433,769 | B2 | 9/2016 | Bayly |
| 9,468,749 | B2 | 10/2016 | Mansour et al. |
| 9,492,649 | B2 | 11/2016 | Carrez et al. |
| 9,636,492 | B2 | 5/2017 | Fangrow, Jr. |
| 9,724,504 | B2 | 8/2017 | Fangrow, Jr. et al. |
| 9,724,505 | B2 | 8/2017 | Williams et al. |
| 9,861,805 | B2 | 1/2018 | Dennis et al. |
| 9,933,094 | B2 | 4/2018 | Fangrow |
| 9,974,939 | B2 | 5/2018 | Fangrow, Jr. |
| 9,974,940 | B2 | 5/2018 | Fangrow, Jr. |
| 10,029,086 | B2 | 7/2018 | Nowak et al. |
| 10,156,306 | B2 | 12/2018 | Fangrow |
| 10,173,045 | B2 | 1/2019 | Mansour |
| 10,179,203 | B1 | 1/2019 | Huslage et al. |
| 10,315,025 | B2 | 6/2019 | Phillips et al. |
| 10,398,887 | B2 | 9/2019 | Fangrow, Jr. et al. |
| 10,441,507 | B2 | 10/2019 | Sanders |
| 10,518,078 | B2 | 12/2019 | Stjernberg Bejhed et al. |
| 10,569,073 | B2 | 2/2020 | Hallisey et al. |
| 10,625,068 | B2 | 4/2020 | Leuthardt et al. |
| 10,655,768 | B2 | 5/2020 | Jones et al. |
| 10,697,570 | B2 | 6/2020 | Fangrow |
| 10,744,315 | B2 | 8/2020 | Sanders |
| 10,842,982 | B2 | 11/2020 | Fangrow, Jr. |
| 10,857,346 | B2 | 12/2020 | Dennis et al. |
| 10,864,362 | B2 | 12/2020 | Jones et al. |
| 10,881,847 | B2 | 1/2021 | Lynn |
| 11,168,818 | B2 | 11/2021 | Fangrow |
| 11,207,514 | B2 | 12/2021 | Kakinoki |
| 11,235,135 | B2 | 2/2022 | Tsai |
| 11,273,297 | B2 | 3/2022 | Kakinoki |
| 11,484,471 | B2 | 11/2022 | Sanders |
| 11,491,084 | B2 | 11/2022 | Ueda et al. |
| 2004/0171993 | A1 * | 9/2004 | Bonaldo ............... A61M 39/26 |
| | | | 604/248 |
| 2004/0215158 | A1 | 10/2004 | Anderson |
| 2005/0090805 | A1 | 4/2005 | Shaw et al. |
| 2006/0129109 | A1 | 6/2006 | Shaw et al. |
| 2007/0088292 | A1 | 4/2007 | Fangrow |
| 2007/0088293 | A1 | 4/2007 | Fangrow |
| 2007/0088294 | A1 | 4/2007 | Fangrow |
| 2007/0225635 | A1 | 9/2007 | Lynn |
| 2008/0039803 | A1 | 2/2008 | Lynn |
| 2010/0037968 | A1 * | 2/2010 | Bisutti .................... F16K 3/085 |
| | | | 137/637.05 |
| 2011/0106046 | A1 | 5/2011 | Hiranuma |
| 2012/0042971 | A1 | 2/2012 | Py |
| 2014/0249487 | A1 | 9/2014 | Lynn |
| 2014/0330254 | A1 | 11/2014 | Rosenberger et al. |
| 2016/0000363 | A1 | 1/2016 | Jones et al. |
| 2018/0161568 | A1 | 6/2018 | Banco et al. |
| 2018/0200147 | A1 | 7/2018 | Sanders |
| 2019/0083772 | A1 * | 3/2019 | Miltenyi ............... A61M 39/18 |
| 2019/0184152 | A1 | 6/2019 | Kakinoki |
| 2019/0282797 | A1 | 9/2019 | Tsai |
| 2020/0113784 | A1 | 4/2020 | Lopez et al. |
| 2020/0179672 | A1 | 6/2020 | Kakinoki |
| 2020/0215319 | A1 | 7/2020 | Fangrow, Jr. et al. |
| 2020/0284385 | A1 | 9/2020 | Fangrow |
| 2020/0323734 | A1 | 10/2020 | Ueda et al. |
| 2020/0338331 | A1 | 10/2020 | Sanders |
| 2021/0069484 | A1 | 3/2021 | Tsai |
| 2021/0077803 | A1 | 3/2021 | Lynn |
| 2021/0252267 | A1 | 8/2021 | Fangrow, Jr. |
| 2021/0388926 | A1 | 12/2021 | Martin et al. |
| 2021/0393938 | A1 | 12/2021 | Lynn et al. |
| 2022/0260189 | A1 | 8/2022 | Deuse |
| 2022/0282814 | A1 | 9/2022 | Fangrow |

FOREIGN PATENT DOCUMENTS

| | | | |
|---|---|---|---|
| EP | 1622675 | B1 | 8/2009 |
| EP | 2144634 | A1 | 1/2010 |
| EP | 2298407 | A1 | 3/2011 |
| EP | 2694132 | A1 | 2/2014 |
| EP | 2562456 | B1 | 6/2014 |
| EP | 2782633 | A1 | 10/2014 |
| EP | 1842002 | B1 | 4/2015 |
| EP | 2736582 | B1 | 5/2015 |
| EP | 2089094 | B1 | 1/2016 |
| EP | 2219721 | B1 | 12/2017 |
| EP | 2753396 | B1 | 12/2017 |
| EP | 2736584 | B1 | 4/2018 |
| EP | 3305361 | A1 | 4/2018 |
| EP | 2271398 | B1 | 11/2018 |
| EP | 2480281 | B1 | 11/2018 |
| EP | 2790750 | B1 | 11/2018 |
| EP | 2331191 | B1 | 3/2019 |
| EP | 3079756 | B1 | 3/2019 |

(56)  References Cited

FOREIGN PATENT DOCUMENTS

| EP | 2121114 | B1 | 5/2019 |
| EP | 2719419 | B1 | 5/2019 |
| EP | 2956204 | B1 | 8/2019 |
| EP | 3421077 | B1 | 8/2019 |
| EP | 3530313 | A1 | 8/2019 |
| EP | 3538201 | A1 | 9/2019 |
| EP | 3570807 | A1 | 11/2019 |
| EP | 3570809 | A1 | 11/2019 |
| EP | 2536463 | B1 | 4/2020 |
| EP | 3381505 | B1 | 5/2020 |
| EP | 3538201 | B1 | 5/2020 |
| EP | 1904152 | B1 | 12/2020 |
| EP | 2150307 | B1 | 12/2020 |
| EP | 3313490 | B1 | 1/2021 |
| EP | 3760275 | A1 | 1/2021 |
| EP | 3851155 | A1 | 7/2021 |
| EP | 3517164 | B1 | 9/2021 |
| EP | 3954355 | A1 | 2/2022 |
| EP | 3960229 | A1 | 3/2022 |
| EP | 3973044 | A1 | 3/2022 |
| EP | 3305361 | B1 | 5/2022 |
| EP | 3134052 | B1 | 8/2022 |
| EP | 3530313 | B1 | 8/2022 |
| WO | WO-2021099437 | A1 | 5/2021 |
| WO | WO-2021180675 | A1 | 9/2021 |
| WO | WO-2021252197 | A1 | 12/2021 |
| WO | WO-2022042956 | A1 | 3/2022 |
| WO | WO-2022149339 | A1 | 7/2022 |
| WO | WO-2022207560 | A1 | 10/2022 |

OTHER PUBLICATIONS

IVTeam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 May 2021 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the Save trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

International Search Report and Written Opinion for Application No. PCT/US2024/019945, dated Jun. 20, 2024, 10 pages.

* cited by examiner

500

100

100

600

TORSIONAL CONNECTOR COUPLING ASSEMBLY

CROSS REFERENCE TO RELATED APPLICATION

This application claims the benefit of priority under 35 U.S.C. § 119 to U.S. Provisional Patent Application Ser. No. 63/454,884, entitled "TORSIONAL CONNECTOR COUPLING ASSEMBLY", filed on Mar. 27, 2023, the entire contents of which is incorporated herein by reference.

FIELD OF THE INVENTION

The present disclosure generally relates to connectors, and, in particular, to connector couplings.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

One or more embodiments of the present disclosure are directed to a coupler including a first connector including a mating portion having a first opening, and a first torsion member disposed within the mating portion and having a first channel, the first torsion member being rotatable relative to the mating portion, and a second connector including a second torsion member having a second channel, and a coupling portion having a second opening and at least partially disposed within the second torsion member, the second torsion member configured to couple to the first torsion member to couple the first connector to the second connector. Rotation of the second torsion member causes rotation of the first torsion member to cause alignment and fluid communication between the first channel, the first opening, the second channel, and the second opening to form a fluid pathway extending from the first connector to the second connector when the first connector is coupled to the second connector. The first connector is configured to decouple from the second connector in response to a pullout force exceeding a predetermined threshold force.

In some embodiments, the coupler further includes a sleeve coupled to the second connector and at least partially surrounding the torsion member, wherein the sleeve is rotatable relative to the coupling portion. The sleeve includes a tab configured to be disposed within a recess of the mating portion to secure the sleeve in an unlocked position when the fluid pathway is formed. The mating portion includes a ring having a recesses configured to receive the tab to secure the sleeve in the unlocked position, the tab has a natural state and a compressed state, the tab being biased to be in the natural state, and securing the tab within the recess results in the tab transitioning from the natural state to the compressed state.

In some embodiments, the sleeve is coupled to the second torsion member such that rotation of the sleeve causes rotation of the second torsion member. The sleeve includes a groove configured to receive a ring of the mating portion when the first connector is coupled to the second connector.

In some embodiments, the pullout force is a force applied to the first connector along a central axis of the first connector and the central axis extends at least along a length of the first connector. The central axis extends through the first connector and the second connector when the first connector is coupled to the second connector.

In some embodiments, the first torsion member and the second torsion member each have a locked position and an unlocked position such that when the first connector is coupled to the second connector, the second torsion member being in the unlocked position causes the first torsion member to be in the unlocked position. The first torsion member and the second torsion member are each biased to be in the locked position.

In some embodiments, the first torsion member is biased to cause the first channel to be unaligned with the first opening.

In some embodiments, the second torsion member is biased to cause the second channel to be unaligned with the second opening.

In some embodiments, the first torsion member includes a key member extending at least partially through the mating portion and the second torsion a key hole sized and shaped to receive the key member to secure the key member within the key hole.

In some embodiments, the second connector includes an outlet portion coupled to the coupling portion, the outlet portion having a channel that extends at least partially into the coupling portion.

In some embodiments, the mating portion includes a first interior space and the coupling portion includes a second interior space such that the first interior space is in fluid communication with the second interior space when the first connector is coupled to the second connector and the fluid pathway is formed.

In some embodiments, the first connector is configured to remain coupled to the second connector when the pullout force does not exceed the predetermined threshold force.

In some embodiments, the coupler has a first configuration and in the first configuration the first connector is coupled to the second connector such that the mating portion is at least partially disposed within the second connector and the fluid pathway is blocked.

In some embodiments, the coupler has a second configuration and in the second configuration the first connector is coupled to the second connector such that the mating portion is at least partially disposed within the second connector and the fluid pathway is formed.

In some embodiments, the coupler has a third configuration and in the third configuration the first connector is decoupled from the second connector and the fluid pathway is blocked.

In some embodiments, the first connector is coupled to a first portion of tubing at the first end and the second connector is coupled to a second portion of tubing at an output portion.

One or more embodiments of the present disclosure are directed to a coupler including a first connector including a first end, a mating portion disposed proximate a second end opposite the first end and having a first opening and a first interior space, and a first torsion member disposed within the first interior space, the first torsion member having a first channel and key member extending through the mating portion, the first torsion member being rotatable relative to the mating portion, wherein the first torsion member has a locked position and a unlocked position, and the first torsion member is biased to be in the locked position, a second connector including a second torsion member having a second channel and a key hole, an output portion having an outlet, a coupling portion having a second interior space and being disposed between the second torsion member and the output portion, the coupling portion having a second opening and being at least partially disposed within the second torsion member, the key hole configured to receive the key member to couple the first connector to the second connector, wherein the second torsion member has a locked position and a unlocked position, and the second torsion member is biased to be in the locked position, and rotation of the second torsion member, which causes rotation of the first torsion member resulting in alignment and fluid communication between the first channel, the first opening, the second channel, and the second opening to form a fluid pathway between the first interior space and the second interior space such that the fluid pathway extends a from the first connector to the second connector when the first connector is coupled to the second connector. The first connector is configured to decouple from the second connector in response to a pullout force exceeding a predetermined threshold force.

One or more embodiments of the present disclosure are directed to a coupler including a first connector including an inlet portion disposed proximate a first end and having an inlet, a mating portion disposed proximate a second end opposite the first end and having a first opening and a first interior space, and a first torsion member disposed within the first interior space, the first torsion member having a first channel and key member extending through the mating portion, the first torsion member being rotatable relative to the mating portion, wherein the first torsion member has a locked position and a unlocked position, and the first torsion member is biased to be in the locked position, a second connector including a second torsion member having a second channel and a key hole, an output portion having an outlet, a coupling portion having a second interior space and being disposed between the second torsion member and the output portion, the coupling portion having a second opening and being at least partially disposed within the second torsion member, the key hole configured to receive the key member to couple the first connector to the second connector, wherein the second torsion member has a locked position and a unlocked position, and the second torsion member is biased to be in the locked position, and a sleeve coupled to and at partially surrounding the second torsion member, the sleeve rotatable relative to the coupling portion such that rotation of the sleeve causes rotation of the second torsion member from the locked position to the unlocked position, the sleeve including a groove configured to receive a ring of the mating portion to secure the sleeve to the mating portion when the first connector is coupled to the second connector. Rotation of the sleeve causes rotation of the second torsion member, which causes rotation of the first torsion member resulting in alignment and fluid communication between the first channel, the first opening, the second channel, and the second opening to form a fluid pathway between the first interior space and the second interior space such that the fluid pathway extends from the first connector to the second connector when the first connector is coupled to the second connector. The first connector is configured to decouple from the second connector in response to a pullout force exceeding a predetermined threshold force.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
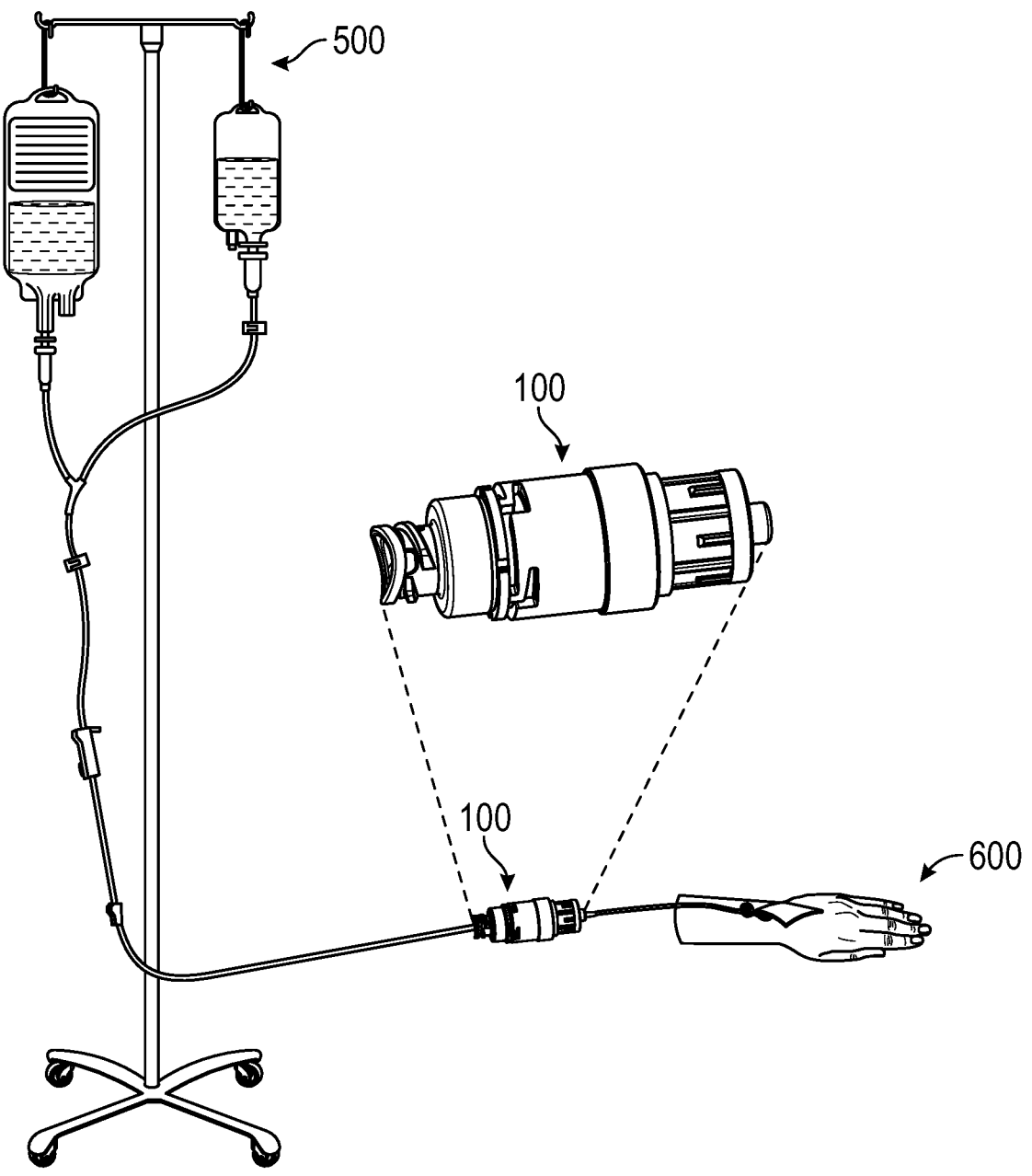
FIG. 1 is a system diagram showing a coupler assembly in use, in accordance with various aspects of the present disclosure.

The disclosed coupler assembly includes a first connector and a second connector. The first connector is configured to couple to the second connector. The coupler assembly may have a first configuration, a second configuration, and a third configuration. In the first configuration, the first connector is coupled to the second connector and a fluid pathway is blocked preventing flow of fluid from the first connector to the second connector. In the second configuration, the first connector is coupled to the second connector and a fluid pathway is formed allowing fluid to flow from the first connector to the second connector. In the third configuration, the first connector is decoupled from the second connector.

The coupler assembly may be configured to couple a first portion of tubing to a second portion of tubing. For example, the first portion of tubing may be coupled to the first connector and the second portion of tubing may be coupled to the second connector. The first portion of tubing and/or the second portion of tubing may also couple to a patient or fluid source. In some embodiments, the coupler assembly allows for the flow of fluid from the first portion of tubing to the second portion of tubing. For example, the first connector may be coupled to the second connector such that a fluid pathway is formed through the first connector and the second connector to allow the flow of fluid from the first portion of tubing through the first connector and the second connector to the second portion of tubing. The fluid pathway may allow for the flow of fluid from the second portion of tubing through the second connector and the first connector to the first portion of tubing.

In some embodiments, the first connector and second connector provide one way fluid flow. For example, when the first connector is coupled to the second connector, fluid may flow from the second connector to the first connector and not from the first connector to the second connector. In some embodiments, decoupling of the first connector from the second connector results in the flow of fluid from the second connector to the first connector ceasing, thereby preventing leakage when the first connector is decoupled from the second connector. In some embodiments, upon decoupling of the first connector from the second connector, the first connector is sterilized (e.g., via a sterilized cloth or a sterilizing device) or replaced with a new sterile connector to prevent infection or contamination that can occur if the first connector is re-used without sterilization. In some embodiments, the first connector is configured to decouple based on a force that exceeds a predetermined threshold force. When a force is applied to the first connector, such as a pullout force, that exceeds the predetermined threshold force, the first connector may decouple from the second connector. The pullout force may be a force that occurs along the longitudinal axis of the first connector. In some embodiments, the pullout force is caused by tugging or pulling on the first portion of tubing coupled to the first connector. Alternatively, the pullout out force applied to the first connector may be caused by tugging or pulling on the second connector and/or the second portion of tubing coupled to the second connector.

In some embodiments, once the first connector is decoupled from the second connector, the first connector is configured to be re-coupled to the second connector. For example, once the first connector decouples from the second connector (e.g., due to a disconnection event), the first connector may be configured to allow for re-coupling to the second connector after a disconnection event.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for case of understanding. Reference numbers may have letter suffixes appended to indicate separate instances of a common element while being referred to generically by the same number without a suffix letter.

While the following description is directed to the connection of medical fittings for the administration of medical fluid using the disclosed coupler, it is to be understood that this description is only an example of usage and does not limit the scope of the claims. Various aspects of the disclosed coupler may be used in any application where it is desirable to secure the connection of various tubing and fittings.

The disclosed coupler assembly overcomes several challenges discovered with respect to certain conventional couplers. One challenge with certain conventional couplers is that certain conventional couplers may be improperly secured. Further, during use, certain conventional couplers may be designed to release or dislodge in response to relatively low pullout forces. For example, certain conventional couplers may release in response to pullout forces experienced during patients rolling over in bed, patients catching tubing or lines on bed rails, moving patients to a different bed, fidgeting by pediatric patients, and/or disoriented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the administration of medical fluids, the use of certain conventional couplers is undesirable.

Therefore, in accordance with the present disclosure, it is advantageous to provide couplers and coupler/connector assemblies as described herein that allows for improved securement of fittings or connectors. The disclosed couplers and coupler/connector assemblies are structured as described herein so as to permit the secure retention of the first connectors, while allowing for decoupling after a disconnection event.

Figure 2:
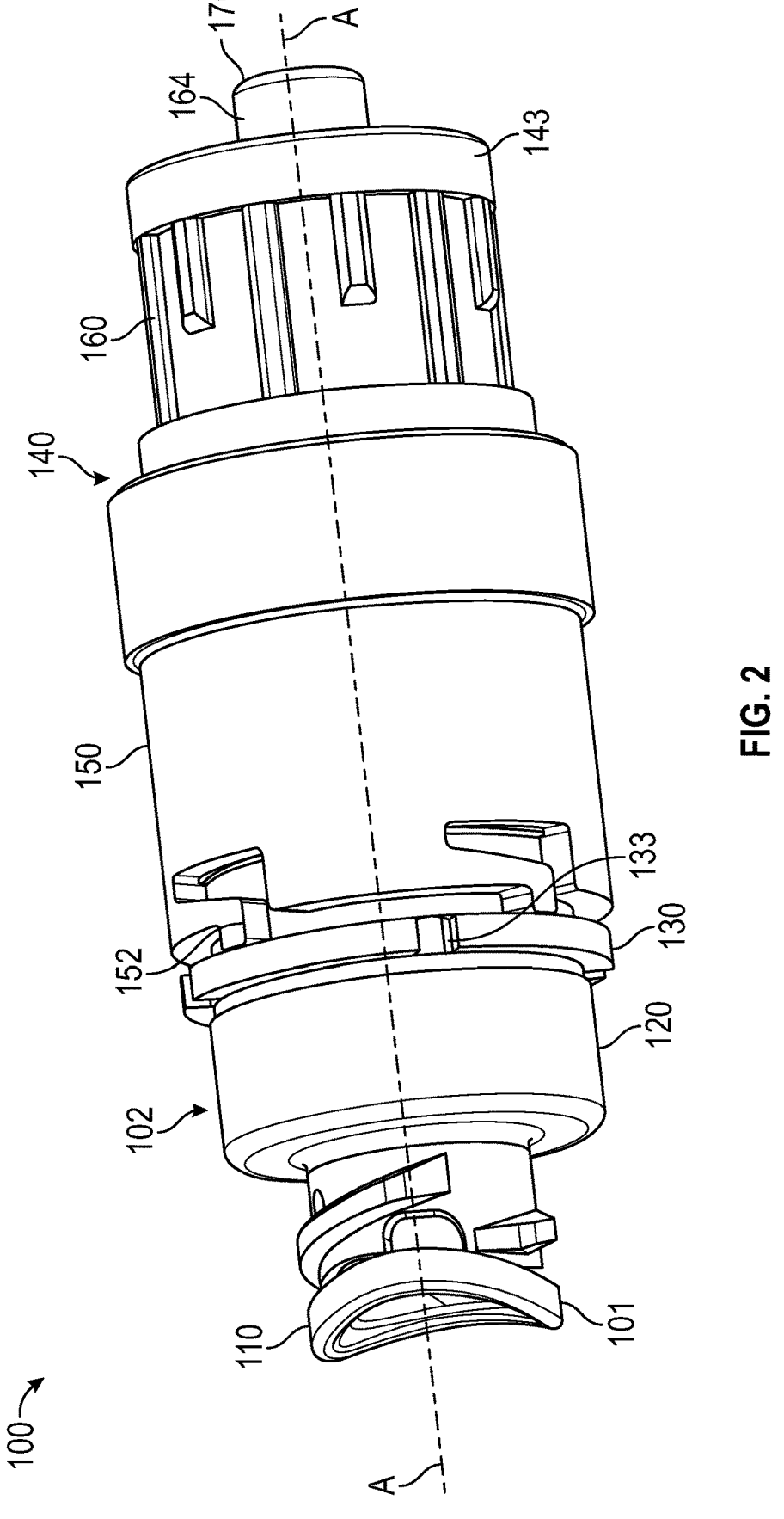
FIG. 2 is a perspective side view of the coupler assembly of FIG. 1 in a first configuration, in accordance with various aspects of the present disclosure.
Figure 3A:
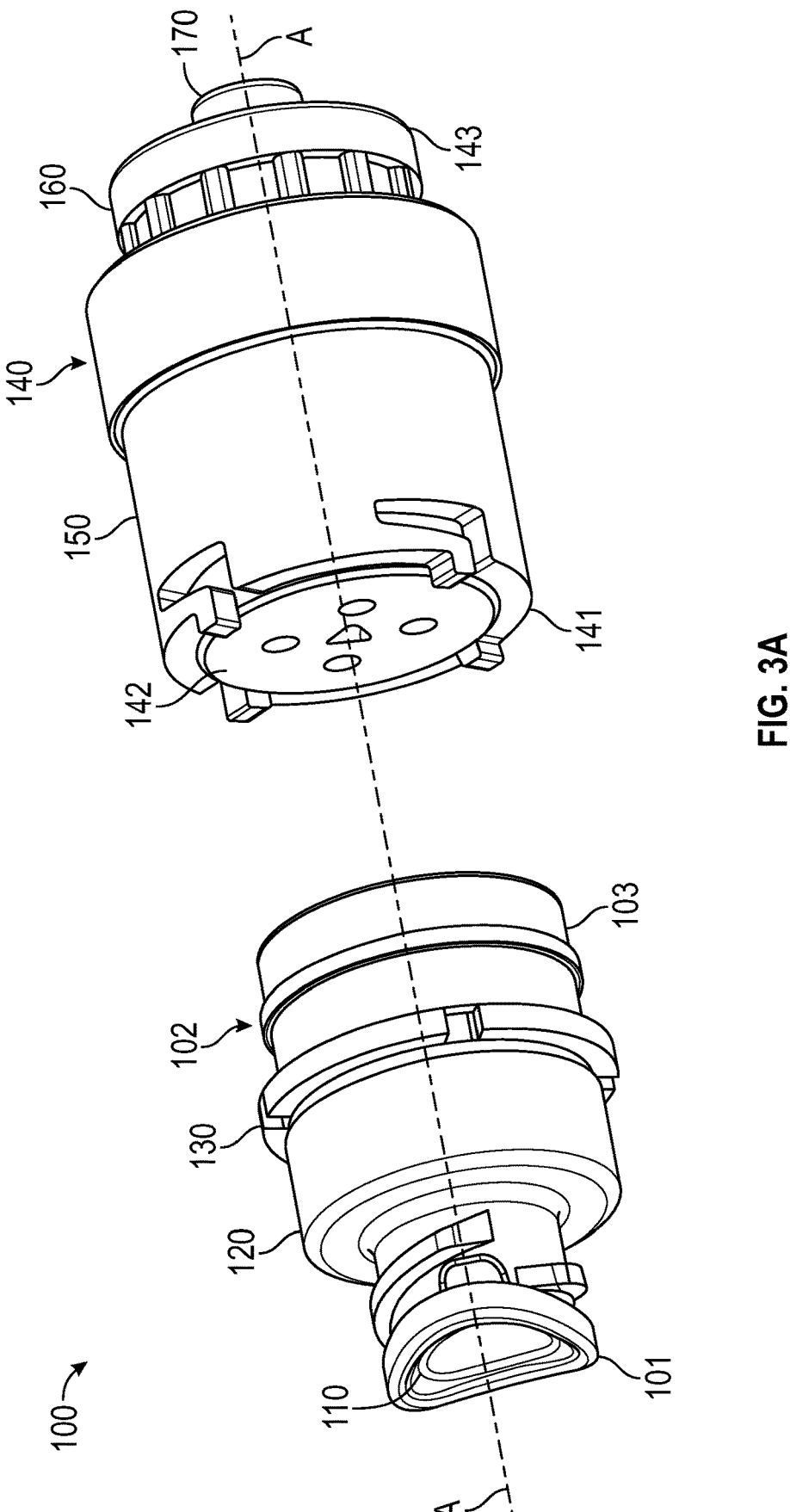
FIG. 3A is a perspective side view of the coupler assembly of FIG. 1 with a first connector decoupled from a second connector, in accordance with various aspects of the present disclosure.
Figure 3B:
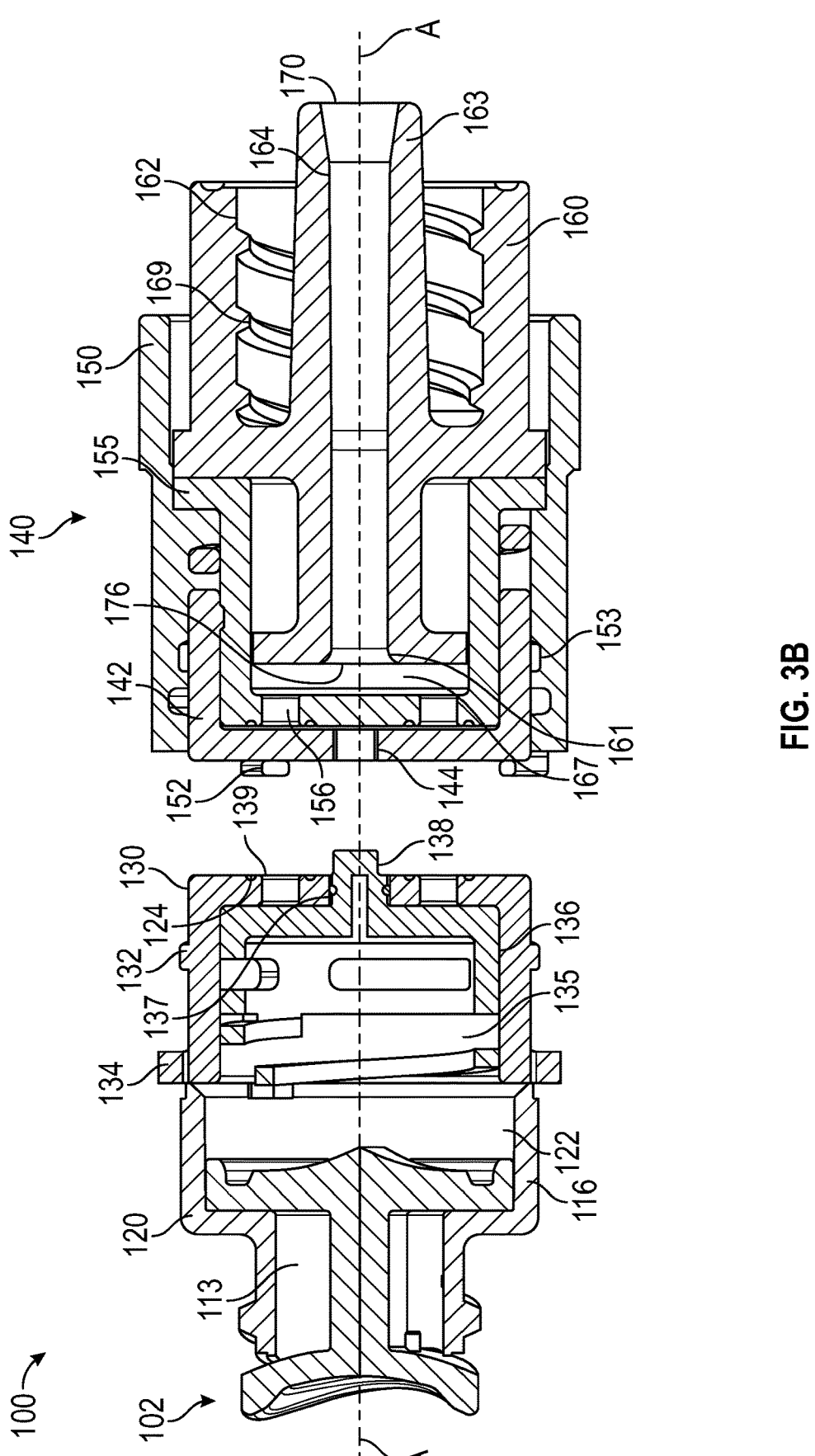
FIG. 3B is a cross-sectional side view of the coupler assembly of FIG. 3A, in accordance with various aspects of the present disclosure.
Figure 4:
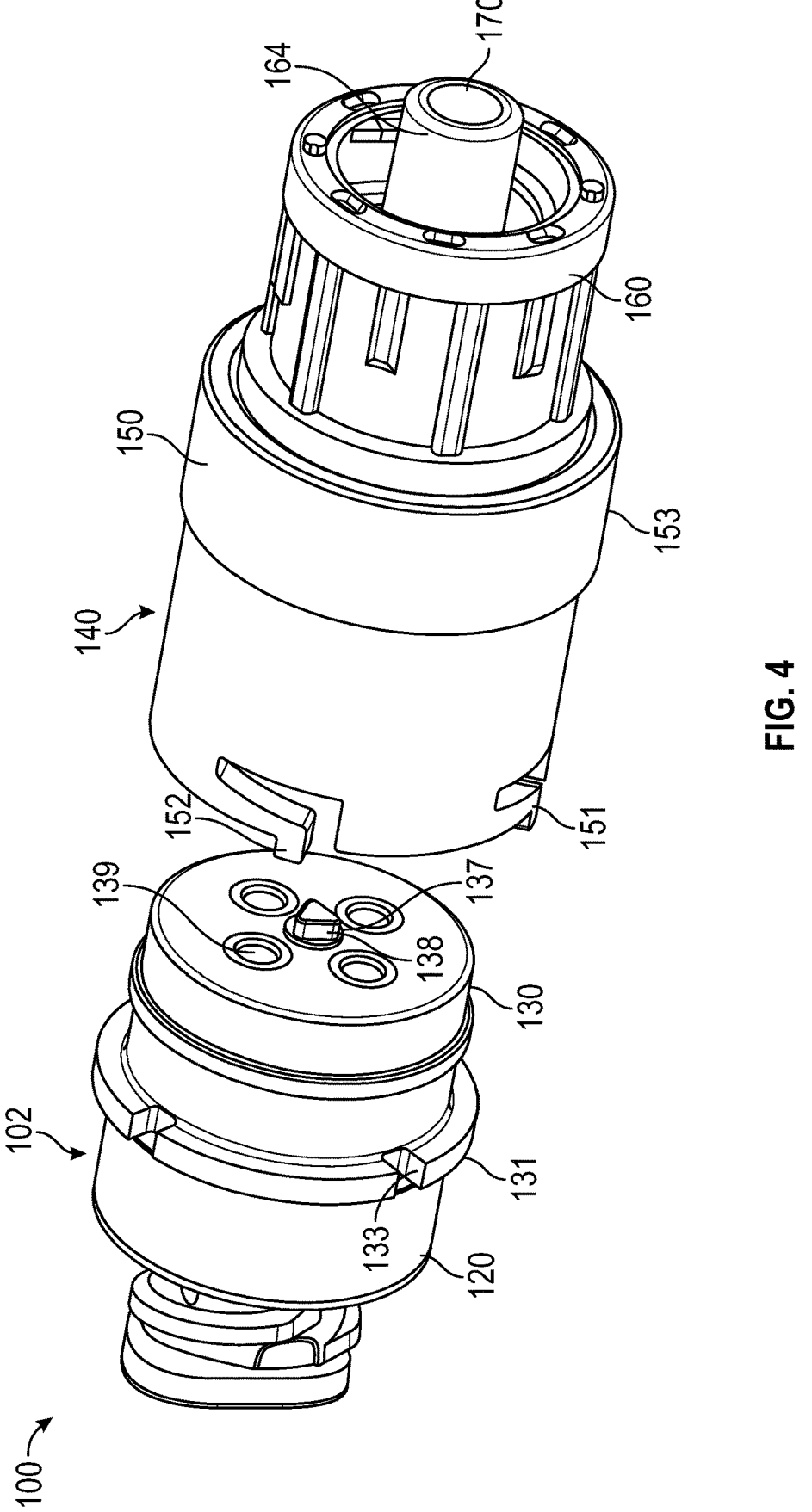
FIG. 4 is a perspective side view of the coupler assembly of FIG. 1 with the first connector decoupled from the second connector, in accordance with various aspects of the present disclosure.

FIG. 1 is a system diagram showing a coupler assembly in use, in accordance with various aspects of the present disclosure. FIG. 2 is a perspective side view of the coupler assembly of FIG. 1 in a first configuration, in accordance with various aspects of the present disclosure. FIG. 3A is a perspective side view of the coupler assembly of FIG. 1 with a first connector decoupled from a second connector, in accordance with various aspects of the present disclosure. FIG. 3B is a cross-sectional side view of the coupler assembly of FIG. 3A, in accordance with various aspects of the present disclosure. FIG. 4 is a perspective side view of the coupler assembly of FIG. 1 with the first connector decoupled from the second connector, in accordance with various aspects of the present disclosure.

With reference to FIGS. 1-4, coupler assembly 100 allows the flow of a fluid, such as a medical fluid, from fluid source 500 to patient end 600 by releasably coupling a portion of tubing or line with another portion of tubing or line in fluid communication. Coupler assembly 100 may include first connector 102 and second connector 140. First connector 102 may be configured to couple to second connector 140. In some embodiments, first connector 102 and/or second connector 140 are one way connectors. In the depicted example, portions of tubing can be terminated with connectors/valves, such as first connector 102 and/or second connector 140. In some embodiments, fluid from fluid source 500 flows through coupler assembly 100 to patient end 600. A cannula or needle may be inserted within a patient at patient end 600 allowing medical fluid to flow from fluid source 500 through coupler assembly 100 and into a patient at patient end 600. In some embodiments, decoupling of first connector 102 from second connector 140 interrupts or prevents flow from fluid source 500 to patient end 600.

In some embodiments, coupler assembly 100 includes central axis A-A and first connector 102 and second connector 140 are coupled in series along central axis A-A. First connector 102 and/or second connector 140 may allow for the connection and/or disconnection of tubing to allow for selective fluid communication therebetween. Central axis A-A may extend longitudinally along the length of first connector 102 and second connector 140.

Figure 6A:
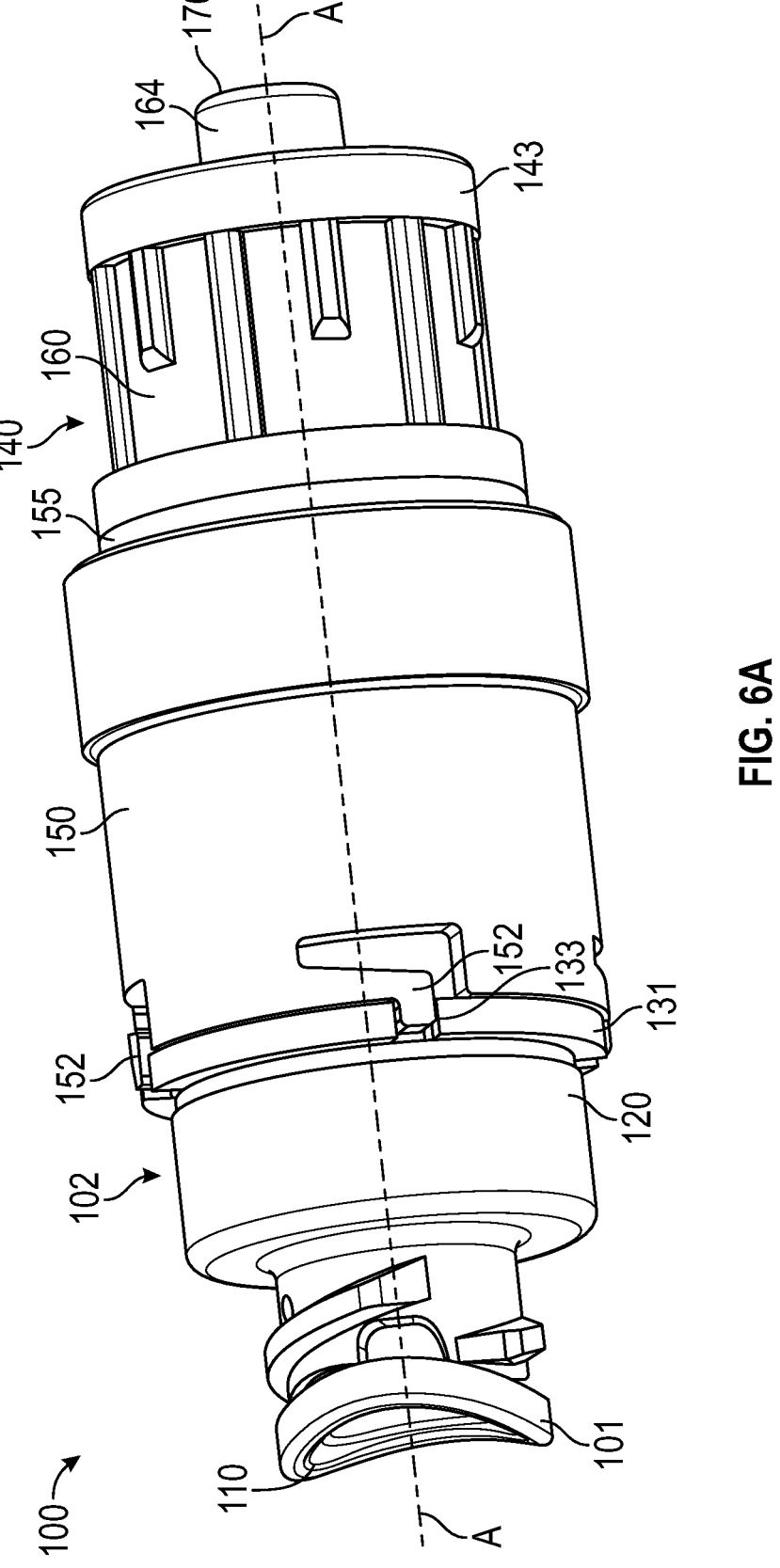
FIG. 6A is a perspective side view of the coupler assembly of FIG. 1 in a second configuration, in accordance with various aspects of the present disclosure.
Figure 7:
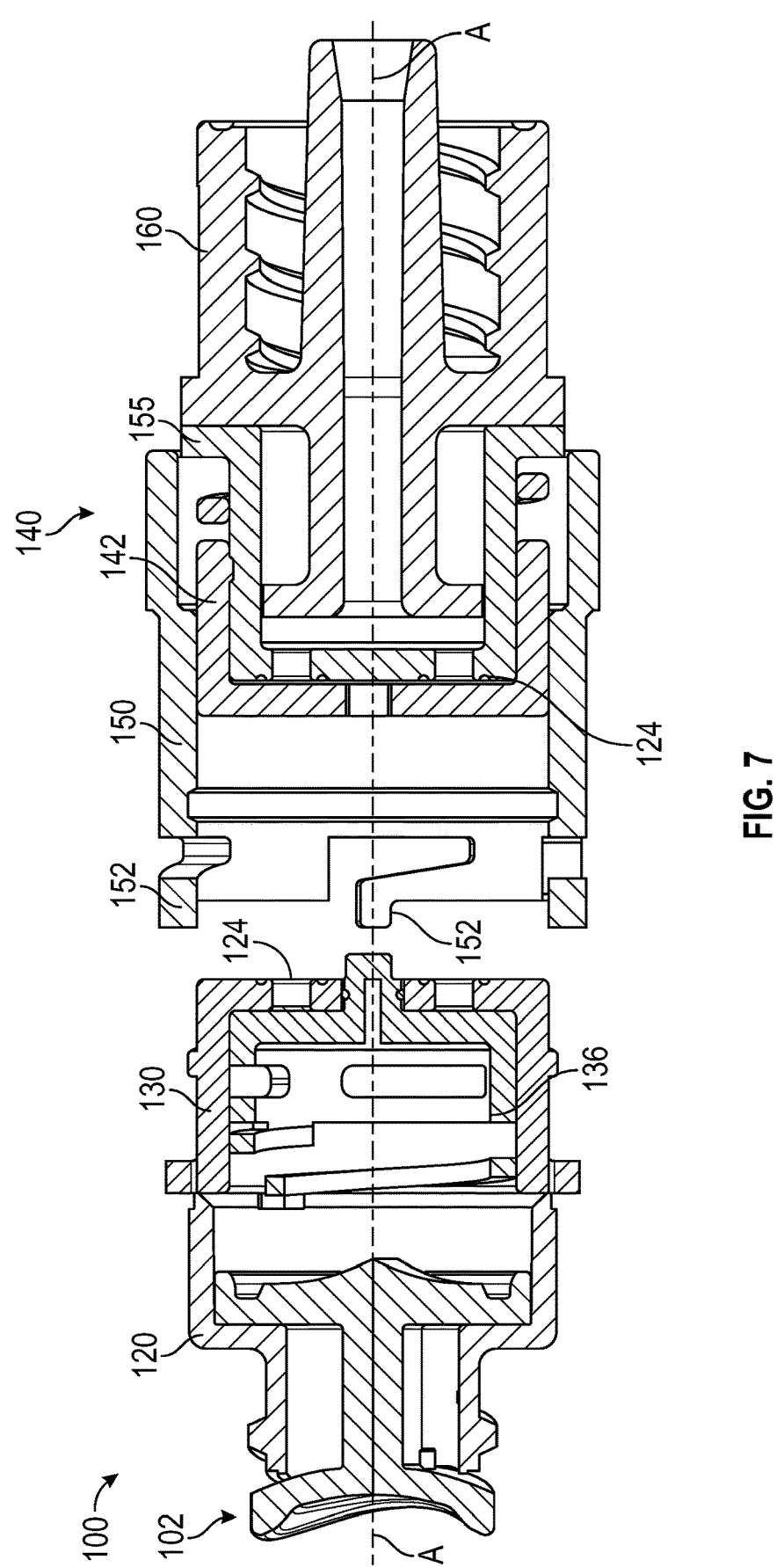
FIG. 7 is a cross-sectional side view of the coupler assembly of FIG. 1 in a third configuration, in accordance with various aspects of the present disclosure.

Coupler assembly 100 may have a first configuration (FIG. 2), a second configuration (FIG. 6A), and a third configuration (FIG. 7). In the first configuration, first connector 102 is coupled to second connector 140 and fluid flow from first connector 102 to second connector 140 is interrupted. In the second configuration, first connector 102 is coupled to second connector 140 and a fluid pathway is formed between first connector 102 and second connector 140 to allow for fluid to flow from first connector 102 to second connector 140. In some embodiments, coupler assembly 100 transitions from the first configuration to the second configuration in response to engagement of a sleeve of second connector 140. In some embodiments, coupler assembly 100 transitions from the second configuration to the third configuration in response to a disconnection event. A disconnection even may occur when a pullout force is applied to first connector 102 causing axial movement of first connector 102 relative to second connector 140. In some embodiments, axial movement of first connector 102 relative to second connector 140 is caused when the pullout force applied to first connector 102 exceeds a predetermined threshold force.

In some embodiments, first connector 102 is coupled to a first portion of tubing to allow the first portion of tubing to be connected and/or disconnected with second connector 140. First connector 102 may include first end 101 and second end 103. First end 101 may be coupled to tubing (e.g., a first portion of tubing) and second end 103 may be configured to couple to second connector 140. For example, second end 103 of first connector 102 may be configured to couple to first end 141 of second connector 140. In some embodiments, a portion of tubing can be coupled with, or engage with first end 101 of first connector 102. First connector 102 via first end 101 may be in fluid communication with the tubing to allow fluid to pass through first connector 102.

In some embodiments, first end 101 can have a flat surface to allow for clinicians to easily clean and disinfect first end 101. First end 101 may be in fluid connection with second end 103. First end 101 and second end 103 may be disposed along the longitudinal length of first connector 102. For example, first end 101 and second end 103 may be disposed along central axis A-A. First end 101 and/or second end 103 may include an opening or channel to allow first end 101 and/or second end 103 to be in fluid communication with one or more elements (e.g., tubing, connectors, valves, collars, attachments, etc.). For example, first end 101 may be coupled to a tube and second end 103 may include one or more openings 139 to allow for fluid communication through first connector 102 and fluid flow out of first connector 102. Openings 139 may be configured to be in fluid communication with openings (e.g., openings 156) of second connector 140 to allow for fluid flow from first connector 102 to second connector 140.

In some embodiments, first connector 102 is configured to couple to second connector 140 such that fluid flows into first connector 102 and out of second connector 140. For example, first connector 102 may include an inlet (e.g., inlet 110) configured to receive fluid and second connector 140 may include an outlet (e.g., outlet 170) configured to allow fluid to exit second connector 140. In some embodiments, first connector 102 being coupled to second connector 140 and coupler assembly 100 being in the second configuration results in the inlet (e.g., inlet 110) of first connector 102 being in fluid communication with the out let (e.g., outlet 170) of second connector 140.

In some embodiments, fluid can exit or flow through first connector 102 via second end 103 disposed opposite to first end 101. The flow path through first connector 102 can have a straight fluid pathway to make flushing easier and to reduce the risk of hemolysis. Optionally, first connector 102 can include features (e.g., raised features, gripping features) disposed on the outer surface of first connector 102 to allow a clinician to more easily handle or manipulate first connector 102. Some embodiments of first connector 102 may provide connectors that are compatible with connectors of other portions of fluid delivery systems. First connector 102 may be substantially cylindrically shaped.

In some embodiments, first connector 102 includes inlet portion 120 disposed proximate first end 101 and mating portion 130 disposed proximate second end 103. Inlet portion 120 may be configured to couple to mating portion 130. In some embodiments, inlet portion 120 and mating portion 130 form a unitary structure, thereby forming first connector 102. Inlet portion 120 may be configured to couple to a portion of tubing allowing first connector 102 to be in fluid communication with the portion of tubing. For example, inlet portion 120 may include inlet 110 configured to allow for fluid to enter inlet portion 120. Inlet portion 120 may also include channel 113 to allow for the flow of fluid within inlet portion 120. Channel 113 may be disposed within inlet portion 120 and extend from first end 101 to body 116 of inlet portion 120.

In some embodiments, mating portion 130 is disposed opposite inlet portion 120 and is configured to couple to second connector 140 to secure first connector 102 to second connector 140. For exampling mating portion 130 may include coupling ring 132 configured to be received by or disposed in groove (e.g., groove 159) of second connector 140 to secure and couple first connector 102 to second connector 140, as described below. Ring 132 may be disposed on mating portion 130 proximate second end 103. In some embodiments, ring 132 is configured to be received by and engage with a corresponding groove (e.g., groove 159) of second connector 140 to secure first connector 102 to second connector 140.

Referring to FIGS. 2-3B, inlet portion 120 may be coupled to mating portion 130 between first end 101 and second end 103. Inlet portion 120 may be disposed proximate first end 101 and may include channel 113 and interior space 117. Channel 113 may lead into interior space 117. For example, channel 113 may be in fluid communication with interior space 117. In some embodiments, a portion of a tube couples to inlet portion 120 such that the portion of the tube is in fluid communication with channel 113. The portion of the tube being in fluid communication with channel 113 also results in the portion of the tube being in fluid communication with interior space 117.

In some embodiments, inlet portion 120 includes body 116. Body 116 may include interior space 122, which may be in fluid communication with channel 113. Channel 113 may have a diameter less than an inner diameter of body 116. In some embodiments, the volume of channel 113 is less than the volume of interior space 122 of body 116. Channel 113 may be in fluid communication with interior space 122 of body 116 such that body 116 (e.g., interior space 117) is configured to hold a larger volume of fluid than channel 113. In some embodiments, interior space 122 is in fluid communication with interior space 135 of mating portion 130.

Mating portion 130 may be disposed proximate second end 103 and may include one or more openings 139, channel 137, interior space 135, and torsion member 136. Interior space 122 of inlet portion 120 may be in fluid communication with interior space 135 of mating portion 130. In some embodiments, fluid flows into inlet 110, through channel 113 into interior space 122 and flows into interior space 135. Openings 139 may be configured to allow for fluid communication with interior space 135. For example, opening 139 may be in fluid communication with interior space 135 to allow fluid to flow from interior space 135 through openings 139.

Torsion member 136 may be disposed within interior space 135. Torsion member 136 may extend from within interior space 135. For example, torsion member 136 may extend the length of mating portion 130. In some embodiments, torsion member 136 is a spring-like structure. For example, torsion member 136 may be biased to be in a locked position. Torsion member 136 may transition from the locked position to an unlocked position in response to a rotational force. Since torsion member 136 is biased to be in the locked position, removal of the rotational force results in torsion member 136 returning to the locked position.

In the locked position, channels 127 (see FIG. 6B) of torsion member 136 may be unaligned or misaligned (e.g., not lined up with) with openings 139. Fluid communication between interior space 135 and openings 139 may be prevented when torsion member 136 is in the locked position due to channels 127 being unaligned or mis aligned with openings 139. Torsion member 136 may transition to an unlocked position thereby aligning channels 127 with openings 139 and allowing fluid communication from interior space 135 and openings 139. Torsion member 136 may transition from the locked position to the unlocked position by rotating torsion member 136 relative to mating portion 130 and inlet portion 120. For example, torsion member 136 may be disposed within interior space 135 of mating portion 130 and may be configured to rotate relative to mating portion 130 to align channels 127 with openings 139.

In some embodiments, torsion member 136 includes key member 138. Key member 138 may extend from torsion member 136 and may be disposed within channel 137 of mating portion 130. Key member 138 may extend from first connector 102 past second end 103. In some embodiments, key member 138 protrudes from first connector 102. Key member 138 being disposed within channel 137 may assist in securing torsion member 136 within interior space 135 of mating portion 130. In some embodiments, key member 138 is configured to be received by a portion of second connector 140 such that rotation of that portion of second connector 140 results in rotation of key member 138 and rotation of torsion member 136 relative to mating portion 130 and inlet portion 120. Rotation of torsion member 136 may result in channels 127 aligning with openings 139. Key member 138 may have a specific shape and a portion of second connector 140 receiving key member 138 may have a corresponding shape to securely receive key member 138.

With continued reference to FIGS. 2-3B, mating portion 130 may include ring 134. Ring 134 may be disposed along an outer circumference or perimeter of mating portion 130. In some embodiments, rings 134 is disposed between first end 101 and second end 103. Ring 134 may be disposed at the junction of inlet portion 120 and mating portion 130. Ring 134 may include one or more recesses 133 configured to receive a portion of second connector 140 (e.g., tab 152). Recess 133 may be configured to receive and secure a portion of second connector 140 (e.g., tab 152) to secure first connector 102 to second connector 140 and keep torsion member 136 in the unlocked position, as described in detail below.

First connector 102 may be configured to couple to second connector 140. Second connector 140 may including torsion member 142, sleeve 150, Coupling portion 155, and output portion 160. Coupling portion 155 may be configured to couple to output portion 160. In some embodiments, coupling portion 155 and output portion 160 form a unitary structure, thereby forming second connector 140.

In some embodiments, second connector 140 is coupled to a second portion of tubing to allow the second portion of tubing to be connected and/or disconnected with first connector 102. Second connector 140 may include first end 141 and second end 143. First end 141 may be configured to couple to first connector 102 and second end 143 may be coupled to tubing (e.g., a second portion of tubing). In some embodiments, a portion of tubing can be coupled with, or engage with second end 143 of second connector 140. Second connector 140 via second end 143 may be in fluid communication with the tubing to allow fluid to pass through second connector 140. In some embodiments, first end 141 can have a flat surface to allow for clinicians to easily clean and disinfect first end 141. First end 141 may be in fluid connection with second end 143. First end 141 and second end 143 may be disposed along the longitudinal length of second connector 140. For example, first end 141 and second end 143 may be disposed along central axis A-A. First end 141 and/or second end 143 may include an opening to allow first end 141 and/or second end 143 to be in fluid communication with one or more elements (e.g., tubing, connectors, valves, collars, attachments, etc.).

In some embodiments, fluid can exit or flow through second connector 140 via second end 143 disposed opposite to first end 141. The flow path through second connector 140 can have a straight fluid pathway to make flushing easier and to reduce the risk of hemolysis. Optionally, second connector 140 can include features (e.g., raised features, gripping features) disposed on the outer surface of second connector 140 to allow a clinician to more easily handle or manipulate second connector 140. Some embodiments of second connector 140 may provide connectors that are compatible with connectors of other portions of fluid delivery systems. Second connector 140 may be substantially cylindrically shaped.

In some embodiments, second connector 140 includes coupling portion 155 disposed proximate first end 141 and output portion 160 disposed proximate second end 143. Output portion 160 may be configured to couple to a portion of tubing allowing second connector 140 to be in fluid communication with the portion of tubing and to a patient via the portion of tubing. For example, output portion 160 may include channel 164 allow for the flow of fluid within output portion 160. Channel 164 may be disposed within output portion 160 and extend the length of output portion 160. In some embodiments, channel 164 extends into coupling portion 155. Channel 164 may include outlet 170. Outlet 170 may be disposed at a distal end of channel 164 and may be disposed proximate second end 143.

In some embodiments, coupling portion 155 is disposed opposite output portion 160 proximate first end 141. Coupling portion 155 may be disposed proximate first connector 102 (e.g., mating portion 130) when first connector 102 is coupled to second connector 140. For example, coupling portion 155 may be configured to be disposed proximate a portion of first connector 102 when first connector 102 is coupled to second connector 140, as described below. Coupling portion 155 may include interior space 167 and one or more openings 156. Openings 156 may be in fluid communication with interior space 167.

In some embodiments, output portion 160 includes channel 164 and tube 162. Channel 164 may extend through tube 162. Channel 164 may include proximal end 163, which may include channel opening 176. Channel 164 may include outlet 170, which may be disposed opposite channel opening 176 and proximal end 163. Channel 164 may allow outlet 170 to be in fluid communication with channel opening 176 such that fluid that enters channel 164 at channel opening 176 (e.g., from first connector 102) flows through channel 164 and out of outlet 170. Tube 162 may be configured to receive and couple to a portion of tubing (e.g., a second portion of tubing). In some embodiments, tube 162 includes grooves 169 disposed on an interior surface of tube 162. Grooves 169 may be configured to assist in securing a portion of tubing within tube 162. For example, a portion of tubing may be inserted into tube 162 and grooves 169 may be configured to assist in preventing the portion of tubing from being inadvertently removed or decoupled from second connector 140.

Coupling portion 155 may be coupled to output portion 160 such that channel 164 extends into interior space 167 of coupling portion 155. In some embodiments, channel opening 176 is disposed within interior space 167. For example, channel opening 176 may be disposed within interior space 167 such that fluid entering openings 156 flows into interior space 167 and into channel opening 176. The fluid may then flow from channel opening 176 to outlet 170 via channel 164.

Second connector 140 may include tension member 142. In some embodiments, torsion member 142 is substantially similar to torsion member 136. torsion member 142 may be coupled to coupling portion 155 and may disposed proximate first end 141. In some embodiments, torsion member 142 is coupled to coupling portion 155 such that coupling portion 155 is at least partially disposed within torsion member 142. In some embodiments, torsion member 142 is a spring-like structure. For example, torsion member 142 may be biased to be in a locked position, similar to torsion member 136. Torsion member 142 may transition from the locked position to an unlocked position in response to a rotational force. Since torsion member 142 is biased to be in the locked position, removal of the rotational force results in torsion member 142 returning to the locked position. In some embodiments, rotating torsion member 142 relative to coupling portion 155 results in torsion member 142 being in the unlocked position, allowing a fluid pathway to be formed from first connector 102 to second connector 140 through torsion member 142.

Torsion member 142 may include channels 147. Channels 147 may allow for fluid communication through torsion member 142. In some embodiments, when first connector 102 is coupled to second connector 140, torsion member 142 is disposed between mating portion 130 and coupling portion 155. Torsion member 142 being in the locked position prevents fluid communication between first connector 102 and second connector 140. For example, torsion member 142 being in the locked position blocks the fluid pathway between openings 139 and openings 156. In the locked position, channels 147 (see FIG. 6B) of torsion member 142 may be unaligned or misaligned with openings 156 of coupling portion 155 thereby block the fluid pathway from first connector 102 to second connector 140.

Figure 5:
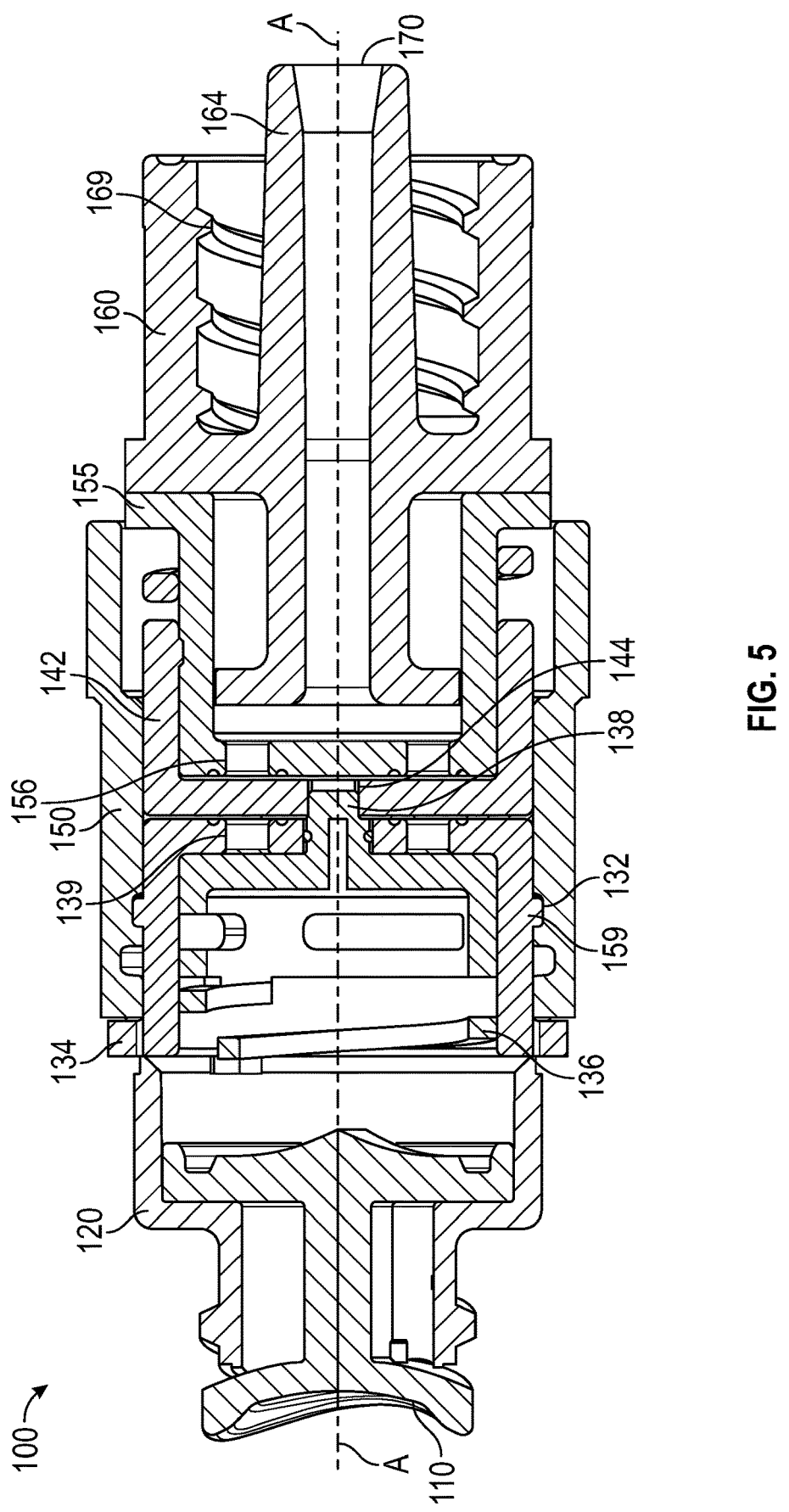
FIG. 5 is a cross-sectional side view of the coupler assembly of FIG. 2, in accordance with various aspects of the present disclosure.
Figures 6B, 6C:
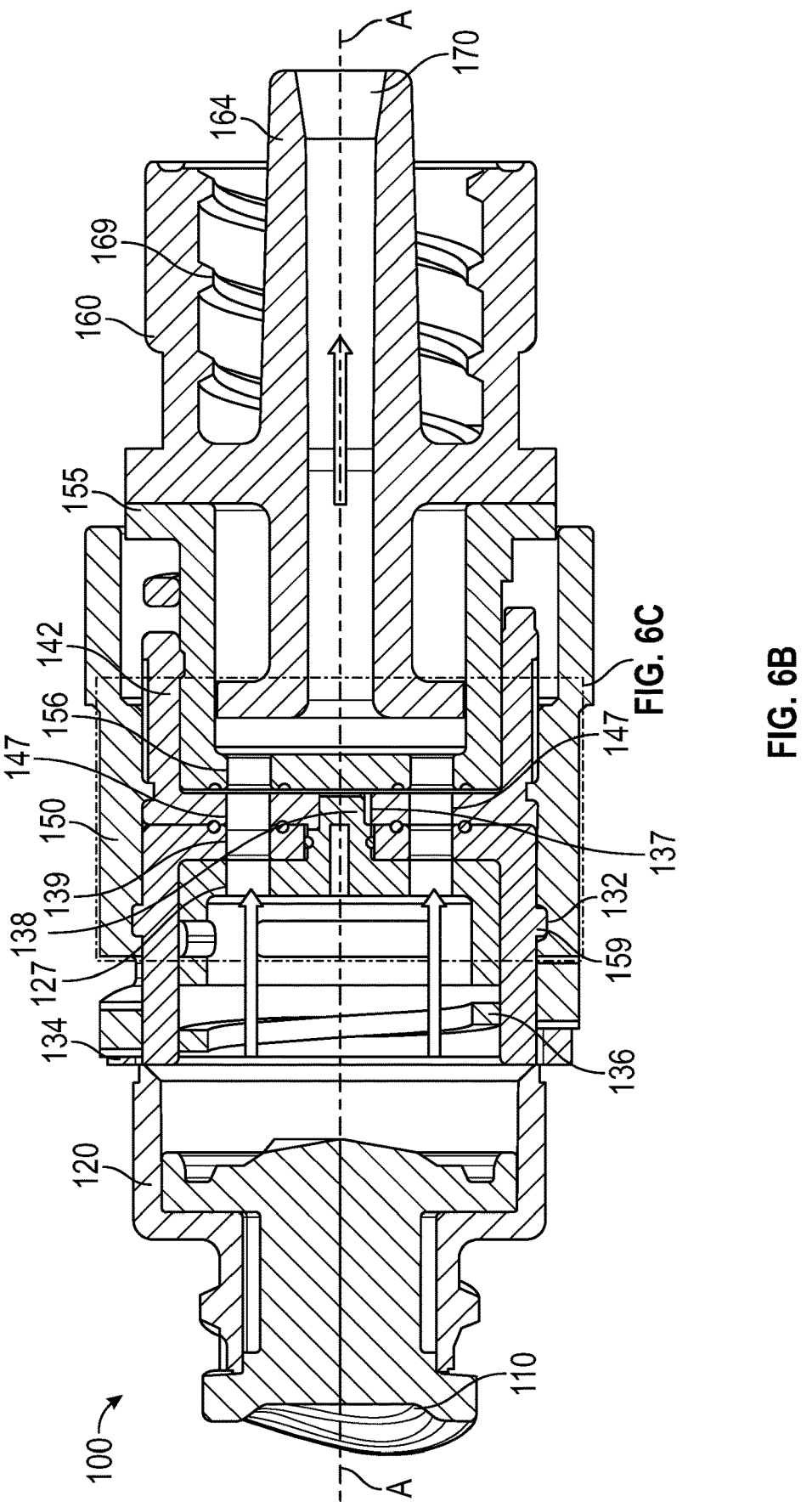
FIG. 6B is a cross-sectional side view of the coupler assembly of FIG. 6A, in accordance with various aspects of the present disclosure.
FIG. 6C is a zoomed in cross-sectional side view of the coupler assembly of FIG. 6A, in accordance with various aspects of the present disclosure.

FIG. 5 is a cross-sectional side view of the coupler assembly of FIG. 2, in accordance with various aspects of the present disclosure. FIG. 6A is a perspective side view of the coupler assembly of FIG. 1 in a second configuration, in accordance with various aspects of the present disclosure. FIG. 6B is a cross-sectional side view of the coupler assembly of FIG. 6A, in accordance with various aspects of the present disclosure. FIG. 6C is a zoomed in cross-sectional side view of the coupler assembly of FIG. 6A, in accordance with various aspects of the present disclosure. FIG. 7 is a cross-sectional side view of the coupler assembly of FIG. 1 in a third configuration, in accordance with various aspects of the present disclosure.

Figure 6C:
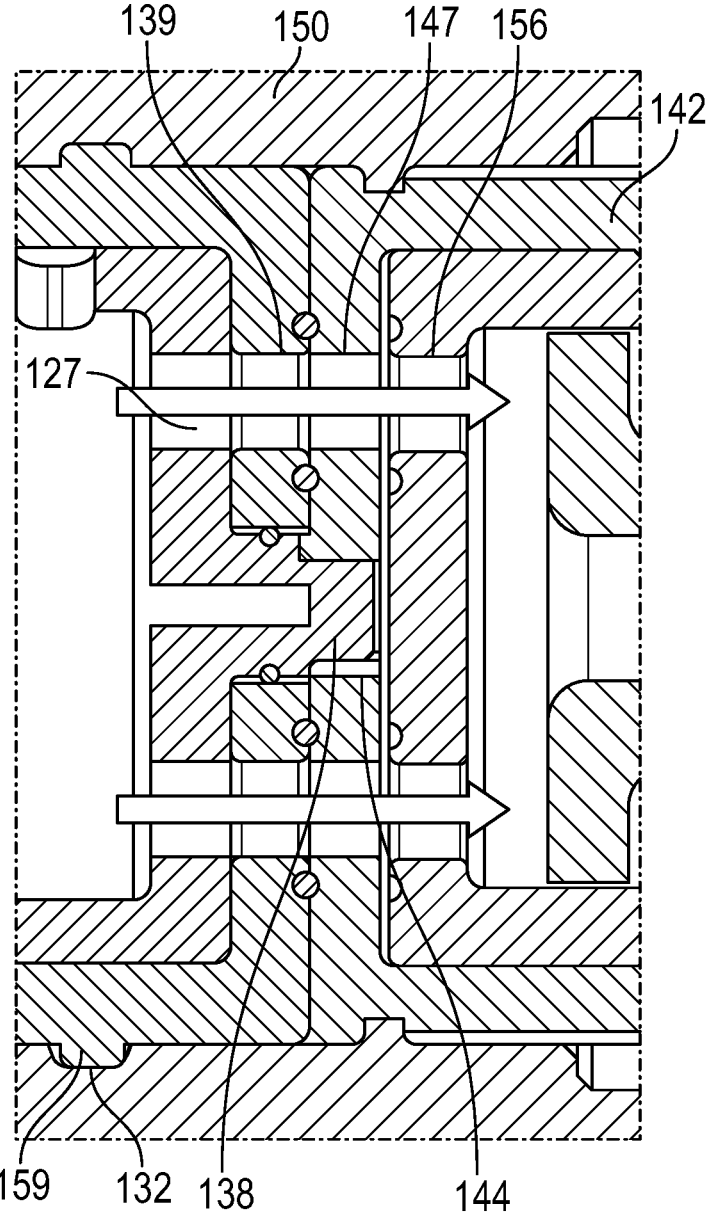

Referring to FIGS. 5-7, when torsion member 142 transitions to the unlocked position (e.g., via rotation of torsion member 142 relative to coupling portion 155), channels 147 align with openings 156. When first connector 102 is coupled to second connector 140 and torsion member 142 is in the unlocked position, channels 147 align with openings 139 and openings 156 to allow for a fluid pathway to form from first connector 102 to second connector 140.

In some embodiments, when first connector 102 is coupled to second connector 140, torsion member 142 being in the unlocked position results in torsion member 136 being in the unlocked position. For example, torsion member 142 may include keyhole 144. Keyhole 144 may be configured to receive key member 138 when first connector 102 is coupled to second connector 140. In some embodiments, coupling first connector 102 to second connector 140 causes key member 138 to align with keyhole 144 such that key member 138 at least partially extends into keyhole 144. Keyhole 144 may be sized and shaped to match the size and shape of key member 138 such that keyhole 144 can receive and secure key member 138 when first connector 102 is coupled to second connector 140.

Key member 138 being inserted and secured within keyhole 144 results in coupling of torsion member 136 to torsion member 142 such that rotation of torsion member 142 causes rotation of torsion member 136. In some embodiments, when torsion member 142 is coupled to torsion member 136, moving torsion member 142 from the locked position to the unlocked position results in torsion member 136 moving from the locked position to the unlocked position. Torsion member 136 and torsion member 142 being coupled together and in the unlocked position allows for a fluid pathway to be formed from first connector 102 to second connector 140.

In some embodiments, torsion member 136 and torsion member 142 being coupled together and in the unlocked position results in channels 127 being aligned with openings 139 and channels 147 being aligned with openings 139 and openings 156 thereby resulting in channels 147 being aligned with channels 127. Channels 127 being aligned with openings 139, channels 147, and openings 156 results in first connector 102 being in fluid communication with second connector 140. For example, when channels 127 are aligned with openings 139, channels 147, and openings 156, fluid may flow from interior space 135 through channels 127, openings 139, channels 147, and openings 156 into interior space 167 and into channel 164. This may result in a fluid pathway being formed between first connector 102 and second connector 140 (FIGS. 6B-6C).

Referring to FIGS. 2 and 5-6C, second connector 140 may include sleeve 150. Sleeve 150 may be disposed around torsion member 142, coupling portion 155, and output portion 160. For example, sleeve 150 may surround torsion member 142 and coupling portion 155. In some embodiments, at least a portion of output portion 160 is disposed within sleeve 150. Sleeve 150 may be configured to move relative to torsion member 142, coupling portion 155, and/or output portion 160. In some embodiments, sleeve 150 is configured to extend past first end 141. For example, sleeve 150 may move along central axis relative to torsion member 142, coupling portion 155, and/or output portion 160 such that sleeve 150 moves between first end 141 and second end 143. In some embodiments, sleeve 150 is configured to be axially locked in place to prevent axial movement. Sleeve 150 may be axially locked in place such that it extends past first end 141 (FIG. 5).

In some embodiments, sleeve 150 can be axially locked in place in multiple positions. For example, sleeve 150 may axially locked in place such that an edge of sleeve 150 is flush with a face of torsion member 142 (FIG. 3A) or such that sleeve 150 extends past first end 141 while still surrounding torsion member 142 (FIG. 5). In some embodiments, sleeve 150 extends past first end 141 such that when first connector 102 is coupled to second connector 140, at least a portion of mating portion 130 is disposed within sleeve 150. Sleeve 150 may be biased to be in an extended position, such that sleeve 150 extends past first end 141 and away from output portion 160.

Sleeve 150 may include groove 159 configured to receive ring 132 of mating portion 130. In some embodiments, when mating portion 130 of first connector 102 is inserted into and disposed within sleeve 150, sleeve 150 may be secured to mating portion 130 by friction fitting ring 132 within groove 159. Disposing ring 132 within groove 159 results in securing sleeve 150 to first connector 102 (e.g., mating portion 130). Ring 132 being secured within groove 159 prevents movement of sleeve 150 along central axis A-A relative to mating portion 130. This reduces inadvertent decoupling of first connector 102 (e.g., mating portion 130) from second connector 140 (e.g., sleeve 150). In some embodiments, ring 132 being disposed within groove 159 allows sleeve 150 to rotate relative to mating portion 130.

In some embodiments, sleeve 150 includes proximal end 151 and distal end 153. Sleeve 150 may include tabs 152 disposed at distal end of sleeve 150. Tabs 152 may be biased towards proximal end 151. For example, tabs 152 may have a natural state and a compressed state. In some embodiments, tabs 152 are configured to be in the compressed state due to application of a pressure to tabs 152. In the compressed state, tabs 152 may be moved towards distal end 153 compared to when tabs 152 are in the natural state. Tabs 152 may include a biasing element to bias tabs in the natural state (e.g., towards proximal end 151).

In some embodiments, sleeve 150 has a locked position (FIG. 2) and an unlocked position (FIG. 6A). Sleeve 150 may be biased to be in the locked position. Application of a rotational force may cause sleeve 150 to transition from the locked position to the unlocked position. In some embodiments, when first connector 102 is coupled to second connector 140, sleeve 150 may be secured in the unlocked position by securing tabs 152 into recesses 133 of ring 134. Securing of tabs 152 within recesses 133 may cause sleeve 150 to remain in the unlocked position. In some embodiments, during rotation of sleeve 150, tabs 152 are pressed against ring 134 resulting tabs 152 being in the compressed state. Sleeve 150 may be rotated until tabs 152 are disposed and secured within recesses 133 resulting in tabs 152 being the natural state. Tabs 152 being disposed and secured within recesses 133 results in securing sleeve 150 in the unlocked position. Sleeve 150 being in the unlocked position causes torsion member 142 to be in the unlocked position. In other words, when sleeve 150 is secured in the unlocked position, torsion member 142 is secured in the unlocked position.

Sleeve 150 may be coupled to torsion member 142 such that rotation of sleeve 150 results in rotation of torsion member 142 to the unlocked position. For example, rotating sleeve 150 relative to coupling portion 155 and/or output portion 160 to be in the unlocked position may result in the rotation of torsion member 142 to the unlocked position. In some embodiments, when first connector 102 is coupled to second connector 140, rotating sleeve 150 relative to coupling portion 155 and/or output portion 160 results in rotating torsion member 142 causing rotation of torsion member 136 due to key member 138 being disposed within keyhole 144. Channels 127 and channels 147 may be aligned such that when channels 127 are aligned with openings 139, channels 147 are aligned with openings 139. Rotation of both torsion member 142 and torsion member 136 due to rotation of sleeve 150 may result in channels 127 aligning with openings 139, channels 147, and openings 156 to cause a fluid pathway to form between first connector 102 and second connector 140.

In some embodiments, a rotational force is applied to sleeve 150 to cause rotation of sleeve 150, which causes rotation of torsion member 142 and torsion member 136. Rotation of torsion member 142 and torsion member 136 may cause torsion member 142 and torsion member 136 to be in the unlocked position. Due to torsion member 142 and torsion member 136 being biased to be in the locked position, removal of the rotational force may cause torsion member 142 and torsion member 136 to return back to the locked position. In some embodiments, securing tabs 152 within recesses 133 when first connector 102 is coupled to second connector 140 results in keeping sleeve 150 (and torsion member 142 and torsion member 136) in the unlocked position. Sleeve 150 (and torsion member 142 and torsion member 136) may transition to back to the locked position when tabs 152 are pushed out of recesses 133 causing sleeve 150 to return back to the locked position since sleeve 150 is biased to be in the locked position.

Referring to FIGS. 6A-6C, sleeve 150 being secured in the unlocked position results in torsion member 142 and torsion member 136 being in the unlocked position and causing a fluid pathway (denoted by arrows in FIG. 6B) to form through first connector 102 and second connector 140. For example, sleeve 150, torsion member 142, and torsion member 136 being in the unlocked position allows for fluid to flow from inlet 110 into interior space 135, through channels 127, openings 139, channels 147, and openings 156, into interior space 167 and through channel 164 to outlet 170.

Coupler assembly 100 may be configured to transition from the first configuration to the second configuration. In the first configuration, first connector 102 is coupled to second connector 140 and sleeve 150 is in the locked position. When coupler assembly 100 is in the first configuration, fluid is prevented from flowing from first connector 102 to second connector 140 since channels 127 are not aligned with openings 139 and thus block openings 139 and channels 147 are not aligned with openings 156 and thus block openings 156. Upon rotation of sleeve 150 to the unlocked position, resulting in torsion member 142 and torsion member 136 being moved to the unlocked position, a fluid pathway between first connector 102 and second connector 140 is formed resulting in coupler assembly 100 being in the second configuration.

Referring to FIG. 7, coupler assembly 100 may be configured to be in a third configuration. In the third configuration, first connector 102 is decoupled from second connector 140. Coupler assembly 100 may transition from the second configuration to the third configuration by moving sleeve 150 to the locked position by removing tabs 152 from being disposed within recesses 133. Removal of tabs 152 from recesses 133 by applying a pressure to tabs 152 toward distal end 153 results in sleeve 150 returning to the locked position since sleeve 150 is biased to be in the locked position. Upon movement of sleeve 150 to the locked position, torsion member 136 and torsion member 142 may transition to the locked position thereby blocking the fluid pathway from first connector 102 to second connector 140. First connector 102 may be decoupled from second connector 140 by removing first connector 102 from being disposed within sleeve 150.

In some embodiments, openings 139 and/or openings 156 include sealing elements 124. Sealing elements 124 may be configured to prevent leakage of fluid from openings 139 and/or openings 156 when first connector 102 is coupled to second connector 140. In some embodiments, sealing elements 124 prevent leakage of fluid from first connector 102 and/or second connector 140. In some embodiments, when the fluid pathway is formed between first connector 102 and second connector 140, sealing elements 124 disposed within or on openings 139 and/or openings 156 prevent leakage or waste of fluid. Sealing elements 124 may be O-rings, adhesives, tubes, or any other type of elements configured to prevent leakage from openings 139 and/or openings 156.

In some embodiments, first connector 102 is configured to decouple from second connector 140 due to a disconnection event, which is caused by a pullout force. For example, a pullout force (e.g., force F) may be applied to first connector 102, either by being directly applied to first connector 102 or indirectly applied to first connector 102, such as being applied to tubing coupled to first connector 102. The pullout force may cause first connector 102 to move axially away from and second connector 140 along central axis A-A thereby decoupling first connector 102 second connector 140. In some embodiments, decoupling first connector 102 from second connector 140 requires removing ring 132 from groove 159. For example, in response to the pullout force, ring 132 may be removed from groove 159 resulting in second connector 140 (e.g., sleeve 150) no longer being coupled and secured to first connector 102 (e.g., mating portion 130).

In some embodiments, application of the pullout force causes tabs 152 to be removed from recesses 133 resulting in sleeve 150 rotating to the locked position due to sleeve 150 being biased to be in the locked position. Upon application of the pullout force, tabs 152 are removed from recesses 133, sleeve 150 rotates to the locked position, and mating portion 130 is removed from being disposed within sleeve 150 thereby decoupling first connector 102 from second connector 140.

In some embodiments, first connector 102 is decoupled second connector 140 when force F exceeds a predetermined threshold force. For example, if force F is less than the predetermined threshold force, first connector 102 may not decouple from second connector 140. The predetermined threshold force prevents inadvertent or accidental decoupling based on minor forces or movements. The predetermined threshold force may be based on the flexibility and/or stiffness of ring 132, groove 159, tabs 152, recesses 133, and/or sleeve 150. For example, the higher the stiffness of ring 132, groove 159, tabs 152, recesses 133, and/or sleeve 150, the higher the predetermined threshold force. In some embodiments, mating portion 130 includes multiple rings 132 disposed at different positions and sleeve 150 includes a corresponding number of grooves 159 to increase the frictional force between mating portion 130 and sleeve 150 to prevent inadvertent decoupling of mating portion 130 (and first connector 102) from second connector 140. In some embodiments, when the pullout force exceeds the predetermined threshold force, ring 132 of mating portion 130 may fail to remain with groove 159 of sleeve 150 thereby permitting decoupling of the first connector 102 from second connector 140.

In some embodiments, the predetermined threshold force is approximately 4 pounds (lbs). The predetermined threshold force may be from approximately 1 lb to approximately 8 lbs, approximately 3 lbs to approximately 7 lbs, approximately 4 lbs to approximately 6 lbs, or greater than 8 lbs. For example, a patient may have a needle/catheter inserted into their skin and the needle/catheter may be coupled to first connector 102 or second connector 140. The patient may walk away from an infusion pump or accidental pull on a fluid line coupled to first connector 102 or second connector 140 and the force exceeds 4 lbs, first connector 102 may automatically release or decouple from second connector 140, effectively closing the fluid pathway between first connector 102 and second connector 140, as described herein.

In some embodiments, upon decoupling of first connector 102 from second connector 140, a user sterilizes first connector 102 and recouples first connector 102 to second connector 140 by inserting mating portion 130 back into sleeve 150 and moving sleeve 150 from the locked position to the unlocked position. In some embodiments, a user may sterilize first connector 102 and/or second connector 140. Recoupling first connector 102 to second connector 140 results in coupler assembly 100 transitioning from the third configuration to the first configuration. Moving sleeve 150 from the locked position to the unlocked position results in coupler assembly 100 transitioning from the second configuration to the third configuration The disclosures described herein include at least the following clauses:

Clause 1: A coupler comprising a first connector including a mating portion having a first opening, and a first torsion member disposed within the mating portion and having a first channel, the first torsion member being rotatable relative to the mating portion, and a second connector including a second torsion member having a second channel, and a coupling portion having a second opening and at least partially disposed within the second torsion member, the second torsion member configured to couple to the first torsion member to couple the first connector to the second connector. Rotation of the second torsion member causes rotation of the first torsion member to cause alignment and fluid communication between the first channel, the first opening, the second channel, and the second opening to form a fluid pathway extending from the first connector to the second connector when the first connector is coupled to the second connector. The first connector is configured to decouple from the second connector in response to a pullout force exceeding a predetermined threshold force.

Clause 2: The coupler of clause 1 further comprising a sleeve coupled to the second connector and at least partially surrounding the torsion member, wherein the sleeve is rotatable relative to the coupling portion.

Clause 3: The coupler of clause 2, wherein the sleeve includes a tab configured to be disposed within a recess of the mating portion to secure the sleeve in an unlocked position when the fluid pathway is formed.

Clause 4: The coupler of clause 3, wherein the mating portion includes a ring having a recesses configured to receive the tab to secure the sleeve in the unlocked position.

Clause 5: The coupler of clause 3, wherein the tab has a natural state and a compressed state, the tab being biased to be in the natural state, and securing the tab within the recess results in the tab transitioning from the natural state to the compressed state.

Clause 6: The coupler of clause 2, wherein the sleeve is coupled to the second torsion member such that rotation of the sleeve causes rotation of the second torsion member.

Clause 7: The coupler of clause 2, wherein the sleeve includes a groove configured to receive a ring of the mating portion when the first connector is coupled to the second connector.

Clause 8: The coupler of clause 1, wherein the pullout force is a force applied to the first connector along a central axis of the first connector and the central axis extends at least along a length of the first connector.

Clause 9: The coupler of clause 8, wherein the central axis extends through the first connector and the second connector when the first connector is coupled to the second connector.

Clause 10: The coupler of clause 1, wherein the first torsion member and the second torsion member each have a locked position and an unlocked position such that when the first connector is coupled to the second connector, the second torsion member being in the unlocked position causes the first torsion member to be in the unlocked position.

Clause 11: The coupler of clause 10, wherein the first torsion member and the second torsion member are each biased to be in the locked position.

Clause 12: The coupler of clause 1, wherein the first torsion member is biased to cause the first channel to be unaligned with the first opening.

Clause 13: The coupler of clause 1, wherein the second torsion member is biased to cause the second channel to be unaligned with the second opening.

Clause 14: The coupler of clause 1, wherein the first torsion member includes a key member extending at least partially through the mating portion and the second torsion a key hole sized and shaped to receive the key member to secure the key member within the key hole.

Clause 15: The coupler of clause 1, wherein the second connector includes an outlet portion coupled to the coupling portion, the outlet portion having a channel that extends at least partially into the coupling portion.

Clause 16: The coupler of clause 1, wherein the mating portion includes a first interior space and the coupling portion includes a second interior space such that the first interior space is in fluid communication with the second interior space when the first connector is coupled to the second connector and the fluid pathway is formed.

Clause 17: The coupler of clause 1, wherein the first connector is configured to remain coupled to the second connector when the pullout force does not exceed the predetermined threshold force.

Clause 18: The coupler of clause 1, wherein the coupler has a first configuration and in the first configuration the first connector is coupled to the second connector such that the mating portion is at least partially disposed within the second connector and the fluid pathway is blocked.

Clause 19: The coupler of clause 1, wherein the coupler has a second configuration and in the second configuration the first connector is coupled to the second connector such that the mating portion is at least partially disposed within the second connector and the fluid pathway is formed.

Clause 20: The coupler of clause 1, wherein the coupler has a third configuration and in the third configuration the first connector is decoupled from the second connector and the fluid pathway is blocked.

Clause 21: The coupler of clause 1, wherein the first connector is coupled to a first portion of tubing at the first end and the second connector is coupled to a second portion of tubing at an output portion.

Clause 22: A coupler comprising a first connector including a first end, a mating portion disposed proximate a second end opposite the first end and having a first opening and a first interior space, and a first torsion member disposed within the first interior space, the first torsion member having a first channel and key member extending through the mating portion, the first torsion member being rotatable relative to the mating portion, wherein the first torsion member has a locked position and a unlocked position, and the first torsion member is biased to be in the locked position, a second connector including a second torsion member having a second channel and a key hole, an output portion having an outlet, a coupling portion having a second interior space and being disposed between the second torsion member and the output portion, the coupling portion having a second opening and being at least partially disposed within the second torsion member, the key hole configured to receive the key member to couple the first connector to the second connector, wherein the second torsion member has a locked position and a unlocked position, and the second torsion member is biased to be in the locked position, and wherein, rotation of the second torsion member, which causes rotation of the first torsion member resulting in alignment and fluid communication between the first channel, the first opening, the second channel, and the second opening to form a fluid pathway between the first interior space and the second interior space such that the fluid pathway extends a from the first connector to the second connector when the first connector is coupled to the second connector. The first connector is configured to decouple from the second connector in response to a pullout force exceeding a predetermined threshold force.

Clause 23: A coupler comprising a first connector including an inlet portion disposed proximate a first end and having an inlet, a mating portion disposed proximate a second end opposite the first end and having a first opening and a first interior space, and a first torsion member disposed within the first interior space, the first torsion member having a first channel and key member extending through the mating portion, the first torsion member being rotatable relative to the mating portion, wherein the first torsion member has a locked position and a unlocked position, and the first torsion member is biased to be in the locked position, a second connector including a second torsion member having a second channel and a key hole, an output portion having an outlet, a coupling portion having a second interior space and being disposed between the second torsion member and the output portion, the coupling portion having a second opening and being at least partially disposed within the second torsion member, the key hole configured to receive the key member to couple the first connector to the second connector, wherein the second torsion member has a locked position and a unlocked position, and the second torsion member is biased to be in the locked position, and a sleeve coupled to and at partially surrounding the second torsion member, the sleeve rotatable relative to the coupling portion such that rotation of the sleeve causes rotation of the second torsion member from the locked position to the unlocked position, the sleeve including a groove configured to receive a ring of the mating portion to secure the sleeve to the mating portion when the first connector is coupled to the second connector. Rotation of the sleeve causes rotation of the second torsion member, which causes rotation of the first torsion member resulting in alignment and fluid communication between the first channel, the first opening, the second channel, and the second opening to form a fluid pathway between the first interior space and the second interior space such that the fluid pathway extends from the first connector to the second connector when the first connector is coupled to the second connector. The first connector is configured to decouple from the second connector in response to a pullout force exceeding a predetermined threshold force.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:
1. A coupler comprising:
a first connector including an inlet, a mating portion having a first opening, and a first torsion member disposed within the mating portion and having a first channel, the first torsion member being rotatable relative to the mating portion; and a second connector including an outlet, a second torsion member having a second channel, a coupling portion having a second opening and at least partially disposed within the second torsion member, and a sleeve at least partially surrounding the second torsion member and rotatable relative to the coupling portion, the second torsion member configured to couple to the first torsion member to couple the first connector to the second connector, wherein rotation of the second torsion member causes rotation of the first torsion member to cause alignment and fluid communication between the first channel, the first opening, the second channel, and the second opening to form a fluid pathway extending from the inlet of the first connector to the outlet of the second connector when the first connector is coupled to the second connector, wherein the first connector is configured to decouple from the second connector in response to a pullout force exceeding a predetermined threshold force.

2. The coupler of claim 1, wherein the sleeve includes one or more tabs, each tab configured to be disposed within a recess of one or more recesses in the mating portion to secure the sleeve in an unlocked position when the fluid pathway is formed.

3. The coupler of claim 2, wherein the mating portion includes a ring having the one or more recesses configured to receive the one or more tabs to secure the sleeve in the unlocked position.

4. The coupler of claim 2, wherein the tab has a natural state and a compressed state, the tab being biased to be in the natural state, and securing the tab within the recess results in the tab transitioning from the natural state to the compressed state.

5. The coupler of claim 1, wherein the sleeve is coupled to the second torsion member such that rotation of the sleeve causes rotation of the second torsion member.

6. The coupler of claim 1, wherein the sleeve includes a groove configured to receive a ring of the mating portion when the first connector is coupled to the second connector.

7. The coupler of claim 1, wherein the pullout force is a force applied to the first connector along a central axis of the first connector and the central axis extends at least along a length of the first connector.

8. The coupler of claim 7, wherein the central axis extends through the first connector and the second connector when the first connector is coupled to the second connector.

9. The coupler of claim 1, wherein the first torsion member and the second torsion member each have a locked position and an unlocked position such that when the first connector is coupled to the second connector, the second torsion member being in the unlocked position causes the first torsion member to be in the unlocked position.

10. The coupler of claim 1, wherein the first torsion member is biased to cause the first channel to be unaligned with the first opening.

11. The coupler of claim 1, wherein the second torsion member is biased to cause the second channel to be unaligned with the second opening.

12. The coupler of claim 1, wherein the first torsion member includes a key member extending at least partially through the mating portion and the second torsion member includes a key hole sized and shaped to receive the key member to secure the key member within the key hole.

13. The coupler of claim 1, wherein the second connector includes an outlet portion coupled to the coupling portion, the outlet portion having a channel that extends at least partially into the coupling portion.

14. The coupler of claim 1, wherein the mating portion includes a first interior space and the coupling portion includes a second interior space such that the first interior space is in fluid communication with the second interior space when the first connector is coupled to the second connector and the fluid pathway is formed.

15. The coupler of claim 1, wherein the coupler has a first configuration and in the first configuration the first connector is coupled to the second connector such that the mating portion is at least partially disposed within the second connector and the fluid pathway is blocked.

16. The coupler of claim 1, wherein the coupler has a second configuration and in the second configuration the first connector is coupled to the second connector such that the mating portion is at least partially disposed within the second connector and the fluid pathway is formed.

17. The coupler of claim 1, wherein the coupler has a third configuration and in the third configuration the first connector is decoupled from the second connector and the fluid pathway is blocked.

18. A coupler comprising:

a first connector including a first end, a mating portion disposed proximate a second end opposite the first end and having a first opening and a first interior space, and a first torsion member disposed within the first interior space, the first torsion member having a first channel and a key member extending through the mating portion, the first torsion member being rotatable relative to the mating portion, wherein the first torsion member has a locked position and an unlocked position, and the first torsion member is biased to be in the locked position;

a second connector including a second torsion member having a second channel and a key hole, an output portion having an outlet, a coupling portion having a second interior space and being disposed between the second torsion member and the output portion, the coupling portion having a second opening and being at least partially disposed within the second torsion member, the key hole configured to receive the key member to couple the first connector to the second connector, wherein the second torsion member has a locked position and an unlocked position, and the second torsion member is biased to be in the locked position; and wherein, rotation of the second torsion member, which causes rotation of the first torsion member resulting in alignment and fluid communication between the first channel, the first opening, the second channel, and the second opening to form a fluid pathway between the first interior space and the second interior space such that the fluid pathway extends from the first connector to the second connector when the first connector is coupled to the second connector, wherein the first connector is configured to decouple from the second connector in response to a pullout force exceeding a predetermined threshold force.

19. A coupler comprising:

a first connector including an inlet portion disposed proximate a first end and having an inlet, a mating portion disposed proximate a second end opposite the first end and having a first opening and a first interior space, and a first torsion member disposed within the first interior space, the first torsion member having a first channel and a key member extending through the mating portion, the first torsion member being rotatable relative to the mating portion, wherein the first torsion member has a locked position and an unlocked position, and the first torsion member is biased to be in the locked position;

a second connector including a second torsion member having a second channel and a key hole, an output portion having an outlet, a coupling portion having a second interior space and being disposed between the second torsion member and the output portion, the coupling portion having a second opening and being at least partially disposed within the second torsion member, the key hole configured to receive the key member to couple the first connector to the second connector, wherein the second torsion member has a locked position and an unlocked position, and the second torsion member is biased to be in the locked position; and a sleeve coupled to and at partially surrounding the second torsion member, the sleeve rotatable relative to the coupling portion such that rotation of the sleeve causes rotation of the second torsion member from the locked position to the unlocked position, the sleeve including a groove configured to receive a ring of the mating portion to secure the sleeve to the mating portion when the first connector is coupled to the second connector, wherein, rotation of the sleeve causes rotation of the second torsion member, which causes rotation of the first torsion member resulting in alignment and fluid communication between the first channel, the first opening, the second channel, and the second opening to form a fluid pathway between the first interior space and the second interior space such that the fluid pathway extends from the first connector to the second connector when the first connector is coupled to the second connector, wherein the first connector is configured to decouple from the second connector in response to a pullout force exceeding a predetermined threshold force.

* * * * *